(12) United States Patent
Pison et al.

(10) Patent No.: US 8,303,931 B2
(45) Date of Patent: Nov. 6, 2012

(54) MULTIMODAL IMAGING USING A THREE COMPARTMENT POLYMER NANOPARTICLE WITH CELL SPECIFICITY

(75) Inventors: Ulrich Pison, Berlin (DE); Bernd-Reiner Paulke, Potsdam (DE); Silvia Pietschmann, Berlin (DE); Regis Cartier, Ingelheim am Rhein (DE); Lutz Kaufner, Berlin (DE)

(73) Assignee: TOPASS GmbH, Berlin (DE)

( * ) Notice: Subject to any disclaimer, the term of this patent is extended or adjusted under 35 U.S.C. 154(b) by 882 days.

(21) Appl. No.: 12/279,695

(22) PCT Filed: Feb. 19, 2007

(86) PCT No.: PCT/EP2007/001567
§ 371 (c)(1),
(2), (4) Date: Jan. 6, 2009

(87) PCT Pub. No.: WO2007/093451
PCT Pub. Date: Aug. 23, 2007

(65) Prior Publication Data
US 2009/0220418 A1     Sep. 3, 2009

(30) Foreign Application Priority Data

Feb. 17, 2006    (EP) .................................... 06090027

(51) Int. Cl.
*A61K 51/00* (2006.01)
*A61M 36/14* (2006.01)

(52) U.S. Cl. ..................... 424/1.29; 424/1.11; 424/1.49; 424/1.61; 424/1.65; 424/1.91; 424/9.3; 424/9.4; 424/9.1; 424/9.6; 977/630; 977/773; 977/927; 977/928

(58) Field of Classification Search .................. 424/1.29
See application file for complete search history.

(56) References Cited

U.S. PATENT DOCUMENTS

| | | |
|---|---|---|
| 2005/0008572 A1 | 1/2005 | Prokop et al. |
| 2005/0201941 A1 | 9/2005 | Cho et al. |
| 2008/0241073 A1 | 10/2008 | Yokoyama et al. |

FOREIGN PATENT DOCUMENTS

| | | |
|---|---|---|
| EP | 0 240 424 A1 | 10/1987 |
| EP | 0240424 A1 | 10/1987 |
| EP | 1 031 354 A2 | 8/2000 |
| WO | 98/58673 A1 | 12/1998 |
| WO | 9918934 | 4/1999 |
| WO | 2004/064109 A2 | 7/2004 |
| WO | 2004/096998 A2 | 11/2004 |
| WO | 2005/112758 A1 | 12/2005 |
| WO | 2006/003731 A1 | 1/2006 |
| WO | 2006/010083 A2 | 1/2006 |

OTHER PUBLICATIONS

Stewart et al. Chem. Mat. 11, 1048-1054.*

* cited by examiner

*Primary Examiner* — Michael G Hartley
*Assistant Examiner* — Sean R Donohue
(74) *Attorney, Agent, or Firm* — Joyce von Natzmer; Agris & von Natzmer LLP

(57) ABSTRACT

The present invention pertains to a three compartment structured polymer nanoparticle (core-shell-corona) for multimodal imaging with specificity for cells or cellular components, thus enabling more advanced diagnostic approaches and targeted therapy on the cellular level without the use of additional biologically active materials.

18 Claims, 9 Drawing Sheets

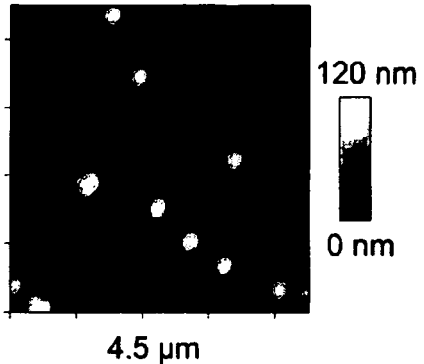

Figure 3:
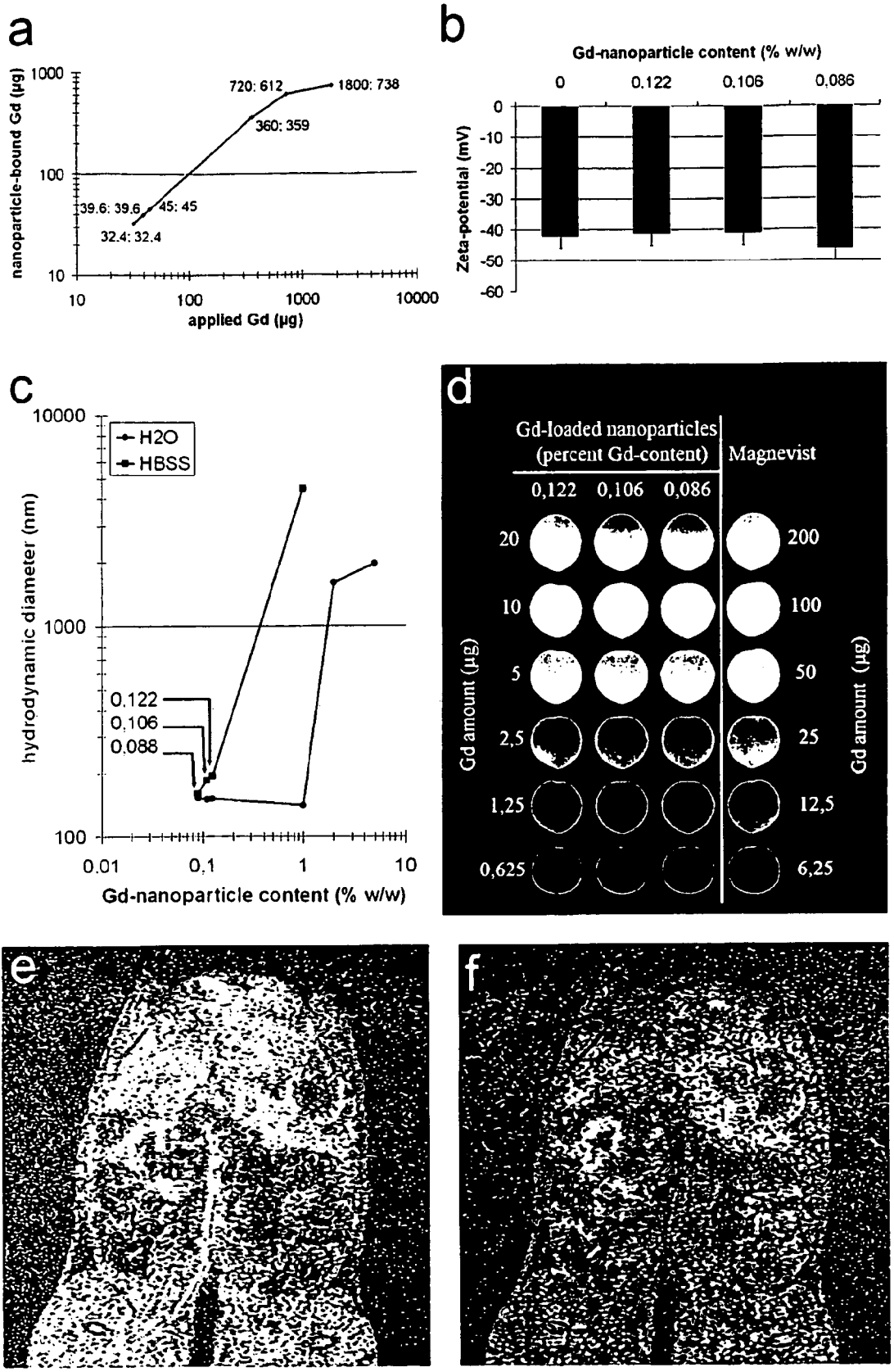

Fig. 1: Size measurements and colloidal stability of polymer nanoparticles.
Atomic Force Microscopy (AFM) of air-dried nanoparticles and Photon Correlation Spectroscopy (PCS) of nanoparticles in aqueous solution were used to determine nanoparticle morphology and hydrodynamic diameter, respectively (n=3). Colloidal stability was assessed by PCS and was defined as the aggregation tendency of nanoparticles under physiological salt condition and pH (Hank's buffered salt solution, HBSS) as well as in HBSS plus 4 % BSA corresponding to the albumin content in the blood.

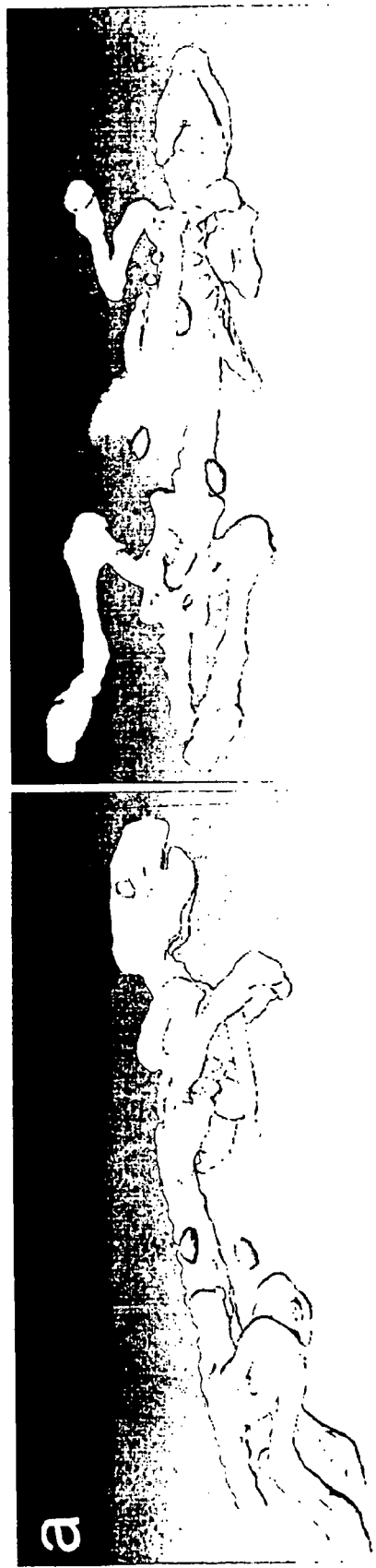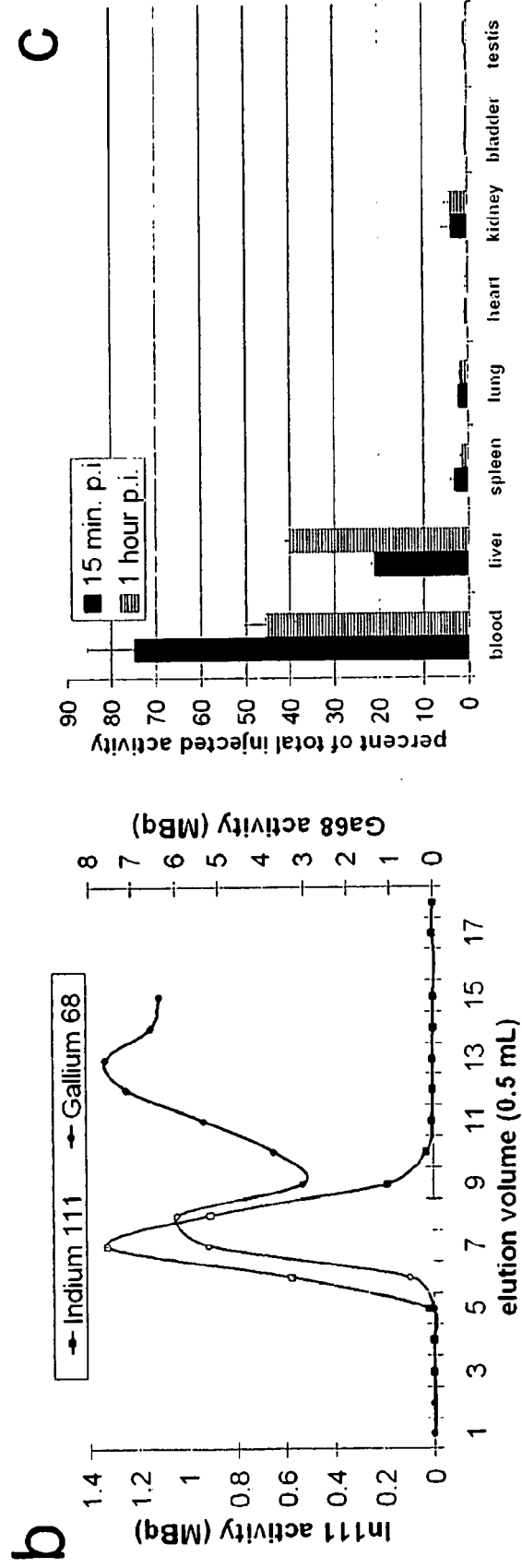
Fig. 2

Fig. 4
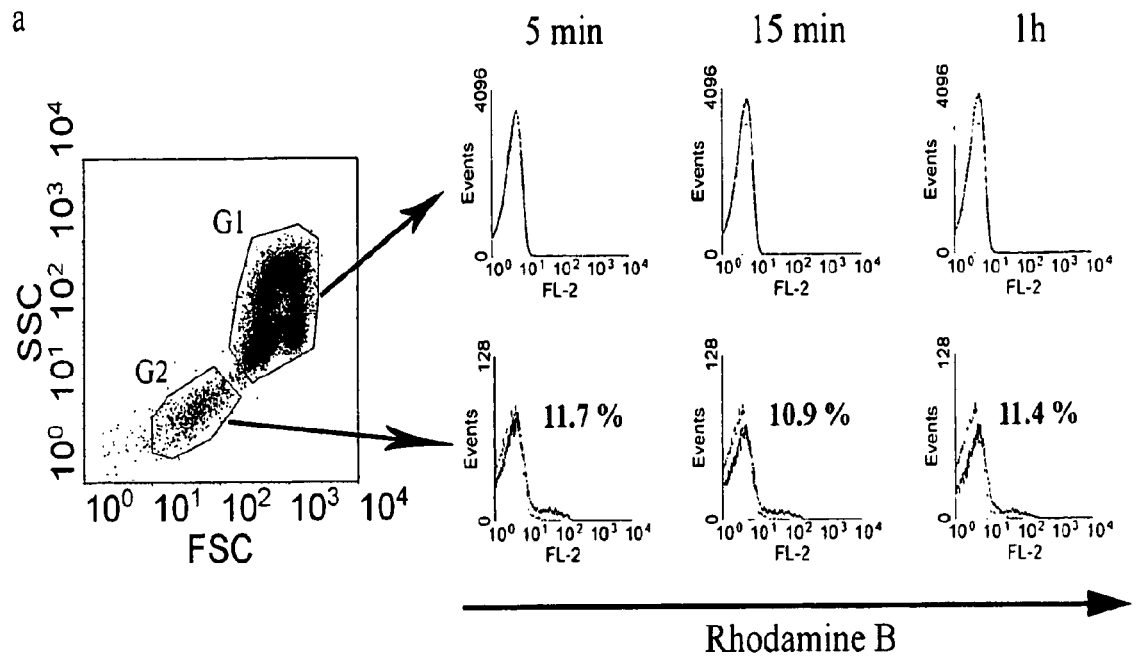
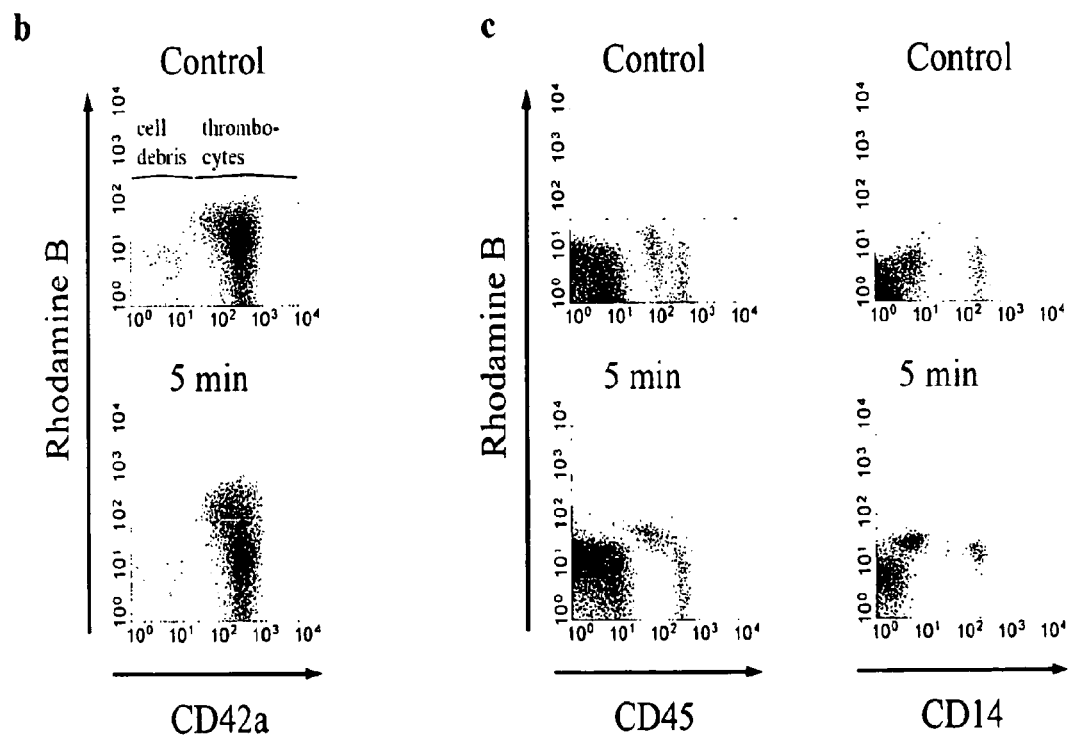

Fig. 9
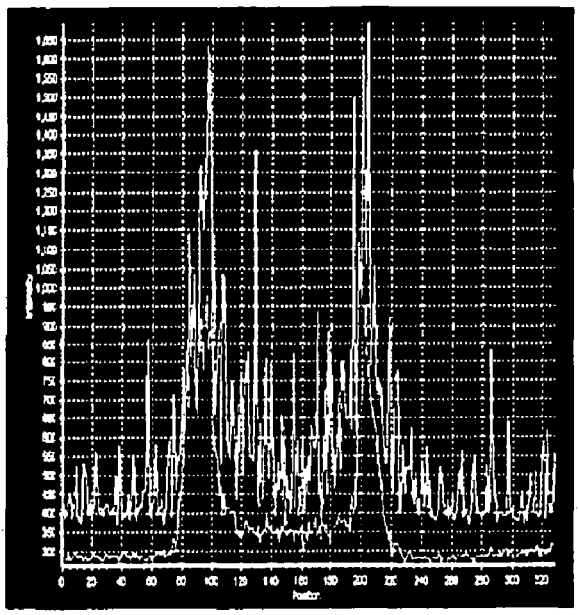

MULTIMODAL IMAGING USING A THREE COMPARTMENT POLYMER NANOPARTICLE WITH CELL SPECIFICITY

CROSS REFERENCE TO RELATED APPLICATIONS

This is the U.S. national stage of International application PCT/EP2007/001567, filed Feb. 19, 2007 designating the United States and claiming priority from European application EP06090027.1, filed Feb. 17, 2006.

FIELD OF THE INVENTION

The present invention pertains to specifically designed polymer nanoparticles with image enhancing properties and cell specificity. These two basic functional properties of polymer particles became possible through controlled monomer addition during polymer particle growth to build a three compartment (core-shell-corona) structure. The outer layer of the particle, the corona, is designed to bind, e.g., CD42a positive cells (thrombocytes) or alternatively CD14 positive cells (monocytes). The intermediate and the inner layer, the hairy shell and the solid core, contain appropriate image enhancing compounds with the following differential localisation to allow multimodal imaging procedures: fluorophores and iron oxide crystals are located in the solid core; gadolinium derivatives, iodine salts and radioisotopes are located in the hairy shell. The resulting polymer nanoparticles may thus be used for imaging procedures including magnetic resonance imaging (MRI) or magnetic particle imaging methods, x-ray imaging, positron emission tomography (PET), gamma scintigraphy, optical imaging techniques, fluorescence activated cell identification and/or sorting procedures, or a multimodal procedure that uses a combination of imaging techniques. The new three compartment polymer nanoparticles enable more advanced diagnostic approaches and targeted therapy on cellular level without using additional biologically active materials.

BACKGROUND OF THE INVENTION AND INTRODUCTION TO THE INVENTION

The synthesis of simple spherical or more sophisticated core-shell polymer nanoparticles is well known in polymer chemistry. Example for the former are latex beads that could be made monodisperse and of various size. Core-shell polymer particle synthesis and structures are deserted by K. Ishizu [46]. A number of parameters have to be met by the polymers to be used in animal and men. Among the most important parameters are that the polymers have to be biocompatible and the final core-shell particle must be colloidal stable in physiological environments such as blood or tissue. Furthermore, half-fife-time of the particle inside the body needs to be long enough to meet diagnostic and/or therapeutic purposes, but as short as possible to keep toxicological burden low.

Image enhancing agents, having a polymeric core including an image-enhancing compound, such as gadolinium that is bound thereto and a polymeric shell surrounding this core-imaging centre have been described by Reynolds et al. [47]. Leverge and Rolland use emulsion polymerisation to prepare simple spherical monodispersed nanoparticles for imaging purposes where the image-enhancing compound is bound to the surface of the particle [48]. In both cases, the descript particles need additional bioreactive or immunoreactive molecules to be cell specific and could not be designed for multimodal imaging due to limited structure-function capabilities.

Scientific literature describes and many patents disclose latex polymers for biomedical applications, and core-shell polymers with advanced functional properties. Most concepts for imaging and targeted therapy using nanoparticles utilises biologically active materials such as monoclonal antibodies manufacturing the appropriate specificity to reach such goals. However, the prior art fails to teach the synthesis of polymer particles for multimodal imaging with specificity for cells or cellular components without the use of additional biologically active materials. To avoid biologically active material such as foreign antibodies is demanding but also of utmost importance in this regard, since the use of biologically active material in patients is risky. In addition, enabling contrast enhanced imaging for different imaging systems (multimodal imaging) would allow to benefit from special advantages of the various systems with only one compound: spatial resolution using magnetic resonance imaging (MRI), sensitivity and specificity using positron emission tomography (PET), temporal resolution using x-ray and computed tomography (CT).

Here, we demonstrate the feasibility of multimodal in vivo imaging and detection using polymer nanoparticles. Cationic tracers such as $^{111}$In, $^{68}$Ga, polyiodinated molecules and Gd were directly bound without the necessity of a chelating conjugates into the hairy shell, the intermediate layer, of polymer nanoparticles. $^{68}$Ga-PET was used as a rapid and non-invasive imaging method to scan the whole animal and revealed the tracer mainly in the heart and the liver and to a less extend in the spleen. $^{111}$In-gamma-scintigraphy of blood and extracted organs demonstrated that this effect was due to localization in the blood compartment. T1-weighted MRI utilising the Gd-label was also achieved and displayed the circulation system. Finally, incorporation of fluorophores such as Rhodamine B into the core of the particles and the use of flow cytometry and confocal microscopy demonstrated rapid association of polymer nanoparticles with thrombocytes and particular leucocytes and monocytes. Thus, the new three compartment polymer nanoparticles enable more advanced diagnostic approaches and targeted therapy on cellular level without the use of additional biologically active materials.

SUMMARY OF THE INVENTION

The present invention pertains to a three compartment structured polymer nanoparticle (core-shell-corona) for multimodal imaging with specificity for cells or cellular components, thus enabling more advanced diagnostic approaches and targeted therapy on the cellular level without the use of additional biologically active materials.

DETAILED DESCRIPTION OF THE INVENTION

Nanoparticle technology is a rapidly emerging field and advanced to clinical applications within the last few years [1-3]. High expectations have been raised for the development of novel high-resolution diagnostics and drug nanocarriers for more efficacious and personalized therapies [4]. The scientific ground was set through our increasing understanding of disease at the molecular level and recent developments in material sciences enabling the production of nanostructured and biocompatible materials.

One obvious advantage in using nanoparticles is to obtain a higher surface to mass ratio of the carrier system permitting relatively high local concentrations of the delivered substances [5]. Colloids also have particular physicochemical properties affecting their pharmacokinetics and in vivo compartmentalization [6]. Unlike soluble substances which generally disseminate from the site of injection and are rapidly cleared by the renal system nanoparticles are usually confined to a particular compartment over a longer period. In addition, chemical functionalization will help to overcome biological barriers or to take advantage of specific transport and degradation processes in order to control the fate of the applied material [7,8].

Over the past years, major efforts concerned studies on nanoparticle toxicity and immunogenicity as well as colloidal stability and blood half-life in the case of intravenous delivery. Another important issue is the controlled delivery of nanoparticles to a particular tissue. Recently, specific tumour targeting was demonstrated in an animal model using isotonic anhydride-modified nanoparticles in comparison to unmodified nanoparticles [9]. It was also noted in this study that 80-90% of the injected material was filtrated by the liver before it could reach the tumour. This illustrates the difficulty to avoid effective clearance by the mononuclear phagocyte system (MPS) and similar results were also shown in other studies [10,11]. The exclusive accumulation of nanoparticles in a targeted tissue is currently a major challenge limiting their broad clinical application and is particularly important when cytotoxic or carcinogenic substances are delivered.

Significant advances could be achieved by a better understanding on the behaviour of nanoparticles in vivo. A critical issue is a more precise localization and detection of the applied material. This could be realized through the concurrent use of various imaging and detection techniques to take advantage of each particular method. The attachment of multiple tracers generally requires the fabrication of multifunctional nanoparticles and one difficulty is to overcome apparent chemical or physicochemical incompatibilities between the different components. $^{68}$Ga is a widely used tracer for positron emission tomography (PET) but requires hydrochloric acid solutions and heat supply for efficient labelling [12]. This poses considerable requirements regarding physical integrity and colloidal stability of the nanoparticles. Further nuclides such as $^{64}$Cu and $^{74}$As are also being tested but they are commercially less available to date [13,14]. Gd is largely used as a contrast enhancer for magnetic resonance imaging (MRI) and has been successfully attached to the surface of latex-nanoparticles as a chelator-complex [15]. However, the relative low payload of Gd achieved at the nanoparticle surface makes in vivo tracking studies difficult. MRI has been realized in vivo using transplanted cells pre-loaded with Gd-labelled nanoparticles [16]. Synthetic dendritic polymers are widely used in biomedical applications [43] and dendritic nanoparticles loaded with Gd or Iodine have been used for MRI [44] or computed tomography (CT) [45], respectively.

Other types of synthetic polymer materials are being developed, among which poly-glycidylmethacrylate (poly-2,3-epoxypropylmethacrylate=EPMA) is well-known in the field of artificial organs or implants [40]. Surface modifications of lattices with EPMA were reported in early studies [41], whereas EPMA homopolymer lattices were developed only recently [17]. The biocompatibility and low toxicity of carboxylated EPMA latex particles was demonstrated in studies showing that nanoparticles with a diameter below 25 nm are taken up by neurites in vivo and subsequently locate in the neuron nucleus following retrograde transport [17-19]. Presently, polymer colloids (or latex particles) are regarded as versatile building block systems to bring a given homo- or copolymer into very different particulate forms. Physicochemical properties such as size and surface charge density can be easily controlled and further chemical groups can be introduced into the polymerization process, for instance for biofunctionalization purposes. In several studies, the fabrication of EPMA-nanoparticles was described, which consist in a compact latex-core with a water-soluble corona composed of protuberant linear polymethacrylic acid strands [20].

It was surprising that the three compartment polymer particles with biocompatible corona and average diameter of between 20 nm and 900 nm show a synergistic effect and that the particles thus do not feature the said disadvantages and are thus suitable for magnetic resonance imaging, x-ray imaging as well as positron emission tomography or gamma scintigraphy.

In a preferred embodiment of the invention, said polymer particles feature a corona made of water soluble polymers with the result of colloidal stability in physiological environments.

In another preferred embodiment of the invention, the polymer particles according to the invention feature a corona which side chains could be cross-linked via chemical activation.

In another preferred embodiment of the invention, the polymer particles according to the invention feature said corona which assembles structures with specific affinity to cells or cellular components, especially to surfaces of peripheral blood cells.

In another preferred embodiment of the invention, the polymer particles according to the invention feature a shell which has high ion exchange capacity to bind paramagnetic metal ions such as gadolinium, suitable for magnetic resonance imaging, to bind opaque material such as polyiodinated or brominated molecules or polymer chains or inorganic materials such as barium sulphate or other metals suitable for x-ray imaging or to bind heavy metal isotopes such as $^{68}$gallium or $^{111}$indium suitable for positron emission tomography or gamma scintigraphy.

In another preferred embodiment of the invention, the polymer particles according to the invention are characterised in that the monomers of the elements forming the shell contain carboxyl and/or hydroxyl groups.

In another preferred embodiment, the polymer particles according to the invention feature a shell which has a hairy structure with high density of carboxyl groups which
(i) bind paramagnetic metal ions such as gadolinium,
(ii) bind opaque material such as polyiodinated or brominated molecules or polymer chains or inorganic materials such as barium sulphate or other metals and/or
(iii) bind heavy metal isotopes such as $^{68}$gallium or $^{111}$indium.

In an even more preferred embodiment of the invention, said shell has a hairy structure with high density of carboxyl groups which bind paramagnetic metal ions such as gadolinium, bind opaque material such as polyiodinated or brominated molecules or polymer chains or inorganic materials such as barium sulphate or other metals and bind heavy metal isotopes such as $^{68}$gallium or $^{111}$indium.

In another preferred embodiment of the invention, the polymer particles according to the invention feature a core which comprises a polymer formed from homopolymers or copolymers with at least one compound selected from the group consisting of acrylic acid, methacrylic acid, methyl methacrylate, 2,3-epoxy-propyl-methacrylate, styrene, ethyl acrylate, butyl acrylate, 2-ethylhexyl acrylate, dimethylaminoethyl methacrylate, tert-butylaminoethyl methacrylate, hydroxyethyl methacrylate, hydroxypropyl methacrylate and vinylacetat.

In another preferred embodiment of the invention, said polymer particles feature said homo- or copolymers which were cross-linked using compound selected from the group consisting of allyl methacrylate (ALMA), ethylene glycol dimethacrylate (EGDMA), trimethylolpropane trimethacrylate (TMPTMA), divinyl benzene (DVB), glycidyl methacrylate, 2,2-dimethylpropane 1,3 diacrylate, 1,3-butylene glycol diacrylate, 1,3-butylene glycol dimethacrylate, 1,4-butanediol diacrylate, diethylene glycol diacrylate, diethylene glycol dimethacrylate, 1,6-hexanediol diacrylate, 1,6-hexanediol dimethacrylate, tripropylene glycol diacrylate, triethylene glycol dimethacrylate, tetraethylene glycol diacrylate, polyethylene glycol 200 diacrylate, tetraethylene glycol dimethacrylate, polyethylene glycol dimethacrylate, ethoxylated bisphenol A diacrylate, ethoxylated bisphenol A dimethacrylate, polyethylene glycol 600 dimethacrylate, poly(butanediol) diacrylate, trimethylolpropane triacrylate, trimethylolpropane trimethacrylate, pentaerythritol triacrylate, trimethylolpropane triethoxy triacrylate, glyceryl propoxy triacrylate, pentaerythritol tetraacrylate, pentaerythritol tetramethacrylate, and dipentaerythritol monohydroxypentaacrylate.

In another preferred embodiment of the invention, the polymer particles according to the invention feature a shell-corona which is preferentially made from monomer units of acrylic acid or methacrylic acid alone or in combination thereof or in combination with monomers of hydroxyethylacrylat or -methacrylate, or polyethylenglykol (PEG)-monomethacrylate.

In another preferred embodiment of the invention, the polymer particles according to the invention feature a total diameter which is smaller than 900 nm, preferentially smaller than 250 nm, and most preferentially smaller than 150 nm.

In another preferred embodiment of the invention, the polymer particles according to the invention are characterised in that the thickness of the corona is between 1 nm and 150 nm.

In another preferred embodiment of the invention, the polymer particles according to the invention are characterised in that the proportion of the core to the total diameter is between 0.1 and 0.995.

The invention also relates to a method of generating an image comprising administering to a subject the image-enhancing agent according to the invention, and subjecting said subject to an image-forming procedure.

In a preferred embodiment of the invention, said image forming procedure is a magnetic resonance and/or magnetic particle imaging procedure, x-ray imaging procedure, positron emission tomography procedure, gamma scintigraphy procedure, optical imaging procedure, fluorescence activated cell identification and/or sorting procedure, or a procedure that uses a combination of these imaging methods.

The invention also relates to the use of polymer particles according to the invention for medical diagnostic purposes to identify diseases of the heart, the circulation, the brain and spinal cord, the bones and joints and cartilage, the lungs, the gastrointestinal tract including liver, spleen, stomach and bowl, pancreas, kidney, ureter, bladder, and the genitals.

In a preferred embodiment of the invention, the polymer particles according to the invention are used for medical diagnostic purposes to identify and monitor neuromuscular diseases, immunological diseases, neoplastic diseases, haematological diseases, neurodegenerative diseases, and inflammatory diseases.

The teachings of the present invention are characterised by the following features:
- departure from the beaten track
- a new perception of the problem
- satisfaction of a long-felt need or want
- hitherto all efforts of experts were in vain
- the simplicity of the solution, which proves inventive action, especially since it replaces a more complex doctrine
- the development of scientific technology followed another direction
- the achievement forwards the development
- misconceptions among experts about the solution of the according problem (prejudice)
- technical progress, such as: improvement, increased performance, price-reduction, saving of time, material, work steps, costs or resources that are difficult to obtain, improved reliability, remedy of defects, improved quality, no maintenance, increased efficiency, better yield, augmentation of technical possibilities, provision of another product, opening of a second way, opening of a new field, first solution for a task, spare product, alternatives, possibility of rationalisation, automation or miniaturisation or enrichment of the pharmaceutical fund
- special choice; since a certain possibility, the result of which was unforeseeable, was chosen among a great number of possibilities, it is a patentable lucky choice
- error in citations
- young field of technology
- combined invention; a combination of a number of known elements, with a surprising effect
- licensing
- praise of experts
- commercial success and
- synergistic effect.

At lease one of said advantages is shown especially in the preferential embodiments of the invention.

It was utterly surprising that three compartment polymer particles (core-shell-corona) do not feature the disadvantages mentioned in the state of the art and can be used both as pharmaceutical products and for a variety of imaging procedures. If the polymer particles according to the invention are not used as pharmaceutical products themselves, in a preferred embodiment of the invention it is possible to bind pharmaceutical products to the polymer particles according to the invention.

Polymer nanoparticle synthesis: All chemicals were used as received. For example, ultra-pure water from a Millipore unit was used for all preparation steps. Polymer nanoparticles were synthesized by a semi-batch emulsion copolymerisation in a 250-mL-double wall glass reactor (HWS Mainz, Germany). This reactor was equipped with glass anchor stirrer, nitrogen inlet, reflux condenser and a dropping funnel. 0.2 g sodium-dodecyl-sulfate (SDS, Serva) was dissolved in 156 mL water. 0.108 g potassium peroxydisulfate (Sigma Aldrich, Seelze, Germany) was dissolved in 20 mL water. 1.6 g methacrylic acid (Fluka/Sigma Aldrich, Seelze, Germany) was dissolved in minimal amount of water and then brought up to a final volume of 20 mL into a plastic syringe (B. Braun) that was hooked up to an infusion pump (type 610 B.S., Medipan Warszawa, Poland). The SDS solution [3.54 mmol/L] was directly given alone into the glass reactor, or in the case of fluorescence-labelling of the nanoparticles (termed as CL2) supplemented with 20 mg Rhodamine B (Sigma Aldrich, Seelze, Germany). Then 18 g of 2,3-epoxypropyl methacrylate (Fluka/Sigma Aldrich, Seelze, Germany) [0.65 mol/L]

was added. The emulsion was purged with nitrogen under continuous stirring (350/min) for 20 min at ambient temperature and then heated to the polymerization temperature of 60'C while purging with nitrogen and stirring was continued. After 10 min at 60° C., the polymerization was started by rapidly adding the potassium peroxydisulfate solution from the dropping funnel into the monomer emulsion inside the reactor [2.04 mmol/L]. At the same time the infusion pump was started with a constant flow rate of 0.15 mL*min$^{-1}$ adding methacrylic acid solution constantly to the polymerizing latex over a period of 2.2 h for carboxylation [0.095 mol/L]. After 6 h the polymerization was finished, the nitrogen stream was stopped and the lattices were cooled down to ambient temperature. The polymer dispersions had a sold content of approximately 10%. Further purification was as follows: Nanoparticles were first dialyzed in VISKING® tubes (exclusion limit 14.000 Dalton) over 3 days against deionised water (100 mL latex against 5 L) with 2 water changes per day. Subsequently, ultrafiltration was performed in 400 mL-BERGHOFF® cells equipped with track-etch membranes (Nuclepore/Whatman; pore size adjusted to the particle size; 25 nm. 50 nm, 100 nm) using ultra-pure water (Millipore) until the filtrate showed an electrical conductivity below 1 µS/cm. All given molar data are related to a final total volume of 196 mL inside the reactor.

Smaller Rhodamine B-labelled polymer nanoparticles (52 nm, termed as CL6) were synthesized by applying 0.7 g SDS and 5 mg Rhodamine B and using 1.2 g of methacrylic acid in the 20 mL syringe (filled with 20 mL aqueous monomer solution). In addition, smaller nanoparticles but with a corona containing both methacrylic acid and polyethylene glycol at equal monomer molarities were also produced (termed as CL13) following the same protocol as for CL6 except that the syringe contained a mixture of 0.6 g methacrylic acid and 1.99 g PEG200-mono-methacrylate.

Polymer nanoparticle labelling and physicochemical characterization: Polymer nanoparticles were labelled for example with $^{111}$In by incubation of 28 mg nanoparticles with $^{111}$InCl$_3$ (Tyco Heafthcare, Germany) containing 6.5 MBq in 1.5 mL deionised water. After 30 minutes labelled nanoparticles were purified by gel filtration using disposable PD 10-desalting columns (Sigma Aldrich, Seelze Germany). Phosphate buffered saline (PBS, Biochrom, Berlin, Germany) was used for column equilibration and elution. Detectable radioactivity was only found in fractions containing eluted nanoparticles indicating that the $^{111}$In was entirely adsorbed on the nanoparticles. After elution, 95% of the loaded nanoparticles could be collected in 1.5 mL resulting in a minimal dilution effect.

$^{68}$Ga was obtained from a 20 mCi $^{68}$Ger/$^{68}$Ga-generator based on TiO$_2$ (Cyclotron Co. Obninsk, Russia). The generated $^{68}$Ga was pre-concentrated using cationic exchange chromatography on a Bio-Rad AG 50W-X8 column (Bio-Rad, Munich, Germany). After binding, the column was washed three times with 80% acetone containing 0.15 M HCl and $^{68}$Ga was eluted with 400 µL 97.56% acetone containing 0.05 M HCl. The generator yielded an amount of 0.3 GBq $^{68}$Ga. Immediately after elution, the acetone was evaporated through a N$_2$-stream for 5 minutes. For the labelling reaction 25 mg polymer nanoparticles in 1 mL deionised water were pre-heated to 82° C. and mixed with the $^{68}$Ga solution. Incubation was prolonged to 15 minutes during which the temperature dropped down to 60° C. Labelled nanoparticles were then purified using a PD 10-column as above. They contained an amount of 0.2 MBq $^{68}$Ga per mg lattice.

For Gd labeling indicated amounts of GdCl$_3$ prepared as a 0.2 mM stock solution were added to 37 mg polymer nanoparticles to a final volume of 1.5 mL and incubated for 30 minutes at room temperature. The amount of Gd bound to the nanoparticles was calculated from the unbound fraction: nanoparticles were sedimented at 20000 g for 5 minutes and the Gd was quantified in the supernatant using a colorimetric assay based on arsenazo III (Sigma Aldrich, Seelze, Germany) [22]. For MRI studies a Gd to nanoparticle amount of less than ~1% (w/w) was used for which no detectable free Gd was found. Consequently, a purification step was omitted following the labelling reaction.

Size of nanoparticles was determined by dynamic light scattering (DLS) and potential was measured by electrophoretic mobility using a Nano-ZS Zetaziser (Malvern Instruments, Herrenberg, Germany) according to the manufacturer's instructions. Three measurements were preformed for each sample and averaged. Indicated results represent the average from three independent preparations. Colloidal stability was defined as the aggregation tendency of nancparticles in various conditions including water, Hank's balanced salt solution at pH 7.4 containing 1 mM MgCl$_2$, 1 mM CaCl$_2$ and 1 g/l glucose (HBSS) and HBSS supplemented with 4% bovine serum albumin (BSA). Briefly, 1 mg nancparticles were diluted in 1 mL indicated media, incubated for 30 minutes at room temperature and measured by DLS. The ξ-potential was determined in 1 mM NaCl. Atomic Force Microscopy (AFM) was performed using a NanoWizard AFM device (JPK Instruments AG, Berlin, Germany) equipped with a microscope (Axiovert 200, Zeiss Jena, Germany). Diluted nanoparticles were briefly incubated on a fresh cleaved mica sheet, rinsed with deionised water and air dried for 5 minutes. Images were taken using the intermitted contact mode using a cantilever tip with a force constant of 7.5 N/m.

In vivo studies: Animal experiments were performed using male Wistar rats (320-350 g body weight) anaesthetized by isoflurane inhalation followed by intraperitoneal injection of 90 mg/kg body weight ketamine hydrochloride (Serumwerk, Bernburg, Germany) and 10 mg/kg body weight xylazine hydrochloride 2% (Bayer, Brunsbütel, Germany) according to the standard animal care guidelines of the state authority for animal research conduct (LaGetSi, Berlin, Germany). Labelled nanoparticles were applied in 500 µL PBS through intravenous injection into a tail vein, if otherwise not indicated.

Positron emission tomography (PET): PET was performed using a MOSAIC Animal PET Imaging system equipped with two SUN Microsystems computer work stations (Philips Medical Systems, Hamburg, Germany) for acquisition and reconstruction of the images. Data were obtained through a step-and-shoot whole body scan in the emission only-acquisition mode, generating 230 slices of 128×128 pixels at 1 mm resolution. Raw data were iteratively reconstructed using the 3D-RAMLA algorithm without attenuation correction. The obtained PET-images were exported in DICOM (Digital Imaging and Communications in Medicine) format and further processed using the Amira™ software package (Mercury Computer Systems, Düsseldorf, Germany). This software permitted 3D visualization of PET-images as well as overlay and alignment of data sets originating from different experiments.

For $^{68}$Ga-PET, polymer nanoparticles containing 2.2 MBq $^{68}$Ga were injected and animals were scanned after 15 minutes. Scan time was 5 minutes during which 7.4 Mega counts (Mcts) were recorded. $^{18}$Fluorine-Fluoride ($^{18}$F-Fluoride) and [$^{18}$F]Fluoro-2-deoxyglucose ($^{18}$FDG) were kindly provided by the Clinic for Nuclear Medicine at the Berlin University Medical School (Charité, Berlin, Germany). For skeleton imaging, rats were injected into the tail vein with 253 MBq $^{18}$F-Fluoridesolution and PET-images were obtained after 5 hours during a 5 minutes scan collecting 106 Mcts. $^{18}$FDG was used as a metabolic tracer for visualization of the eyes, heart and kidney. 62 MBq $^{18}$FDG were injected into the tail vein and animals were scanned after 25 minutes. 55 Mcts were collected during 3 minutes.

Magnetic Resonance Imaging (MRI): MRI was performed using a 3 T-MR scanner (Signa Excite 3.0T, General Electric Healthcare, Milwaukee, USA) equipped with a 40 mT/m gradient system and an extremity coil. For phantom imaging indicated amounts of Gd-labelled polymer nanoparticles or Magnevist™ as a control contrast agent (Schering, Berlin, Germany) were diluted in 1 mL PBS and dispensed in Nunc 24 micro well plates (Sigma Aldrich, Seelze, Germany). MR scans were performed with a T1-weighted spinecho (SE) pulse sequence (TR/TE=540 ms/18 ms, spatial resolution 0.37×0.43×1.0 mm, NEX=4). For in vivo imaging rats were intravenously injected with 1 mL containing 25 mg nanoparticles carrying 21.5 µg Gd. Commencing immediately after injection 6 consecutive fat-suppressed abdominal MR scans within periods of 30 seconds employing the method of time-resolved imaging of contrast kinetics (TRICKS) [23] were performed.

Gamma Scintigraphy: Gamma scintigraphy was used for quantitative biodistribution studies of $^{111}$In-labeled polymer nanoparticles. 15 minutes or 1 hour after nanoparticle application animals were sacrificed by intravenous injection of 200 mg/kg body weight ketamine hydrochloride. A blood sample of 1 mL was immediately taken through heart puncture, organs were subsequently removed and rinsed in PBS. Radioactivity was measured in a 1480 Wallac WIZARD™ Gamma Counter (PerkinElmer, Rodgau-Jügesheim, Germany). The total activity in the blood was calculated assuming a rat blood volume of 60 mL per kg body weight. Indicated values are averaged data from 4 independent experiments.

Flow cytometry and fluorescence microscopy: To analyze interaction of Rhodamine B-labelled polymer nanoparticles with blood components 200 µL whole blood from healthy human donors were mixed with 5 µL nanoparticles (120 µg). This nanoparticle to blood ratio corresponded to the average nanoparticle dilution factor in the animal experiments. The mixture was incubated at 37° C. and samples were diluted 100-fold in PBS at indicated time points. In some experiments incubation was performed at room temperature (RD or at 4° C. using pre-cooled blood. For competition experiments the whole blood was incubated with a first nanoparticle type using the indicated temperature and incubation time. A second nanoparticle type was then added as a binding competitor and the mixture was further incubated as indicated. Diluted cells were immediately run for 90 seconds on a FACScan flow cytometer equipped with a 488 nm argon laser (Becton-Dickinson, Heidelberg, Germany) and data were analyzed using CellQuest Software. The logarithmic scattered plot was set to distinguish between two populations, one containing thrombocytes and cell debris and the other erythrocytes and leucocytes. Both populations were gated to perform fluorescence measurements in the FL-2 channel. Considering that the rat blood contains $5 \times 10^9$ erythrocytes per mL and that 510000 erythrocytes were counted during the run the total analyzed blood volume was estimated to 0.1 µL. To further distinguish thrombocytes from cell debris direct immunofluorescence staining was performed using a FITC-labelled anti-CD42a-antibody (BD PharMingen, Heidelberg, Germany). The same experimental protocol was used as above except that 5 minutes after adding the nanoparticles 4 µL of the antibody were added to the mature and incubated for 10 minutes at room temperature in the dark. After dilution with PBS the thrombocyte/cell debris population was gated as described and Rhodamine B- and FITC fluorescence were measured in the FL-2- and FL-1 channel, respectively.

Similarly, interaction of Rhodamine B-labelled nanoparticles with leucocytes was analyzed using immunostaining of the leukocyte common antigen CD45 or the monocyte surface antigen CD14. In these experiments 2.5 µL nanoparticles were incubated with 100 µL whole blood for 5 minutes at room temperature and 2 µL FITC-labelled anti-CD45 (BD PharMingen, Heidelberg, Germany) or FITC-labelled anti CD14-antibody (Beckman Coulter, Krefeld, Germany) were added. After 10 minutes 500 µL OptiLyseC solution (Beckman Coulter, Krefeld, Germany) were added and the mixture was further incubated for 10 minutes to permit erythrocyte lysis and leukocyte fixation. Finally, 500 µL PBS was added to the samples and flow cytometry was performed directly after 5 minutes. Fluorescence was measured as described. In the case when association of leucocytes with thrombocytes was measured, the whole blood was incubated with the FITC-labelled anti CD42a-antibody as above and cells were gated to discriminate thrombocytes and select leucocytes only.

For cell culture experiments J 774-A1 cells (mouse monocyte macrophages ACC 170; German Collection of Microorganisms and Cell Cultures) and human monocytic THP-1 cells were grown in Dulbecco's MEM medium containing 10% fetal bovine albumin (Boehringer, Germany) at 37° C. in 5% $CO_2$. For cell uptake studies $2 \times 10^5$ cells were incubated with 300 µg nanoparticles in 500 µL growth medium for 15 minutes at 37° C. Cells were washed twice with PBS buffer and observed using an inverted fluorescent microscope (Axiovert 200M, Zeiss, Germany) equipped with the Axiovision 3.1 software. For microscopic observations of thrombocytes, whole blood was incubated with the nanoparticles, thrombocytes were then stained using the anti CD42a-antibody and blood was lysed as for the leukocyte flow cytometric experiment described above. For all experiments representative data from 3 independent experiments are shown.

Synthesis and radiolabelling of polymer nanoparticles: Polymer nanoparticles are easily synthesized by emulsion copolymerization and different types were produced that differ in size, polymer hydrophilicity and surface coverage with functional groups. Fluorescent molecules and/or iron oxide crystals can be added by inclusion polymerization and colloidal properties of the resulting lattices can be varied through surface extensions using appropriate polymers. In addition, their biocompatibility has been proved in several animal studies [17-21].

We wanted to use $^{68}$Ga-PET as a sensitive and non-invasive detection method to study the biodistribution of polymer nanoparticles and therefore, selected a particle type that would be resistant to acidic treatment and heat supply. The resulting nanoparticles carry a polymethacrylate corona and exhibit physical and colloidal stability at pH 1 and 80'C. The hydrodynamic diameter is 144 nm with a narrowed polydispersity index of 0.012. Atomic Force Microscopy observations of dried nanoparticles showed a monodisperse population of around 120 nm sized spheres. The nanoparticles have a strong negative ξ-potential (−421 mV, FIG. 2(b)) that can be attributed to the high surface density of carboxyl groups. Colloidal stability was verified in buffered salt solution approximating in vivo conditions regarding pH, ionic strength and content in divalent cations (HBSS). Furthermore, adsorption of serum albumin was not detected as assessed by dynamic light scattering experiments. Because of their size, ξ-potential and colloidal stability we thus concluded that polymer nanoparticles meet basic physicochemical requirements for intravenous delivery.

The PET-tracer $^{68}$Ga is a trivalent metal cation usually complexed to a chelator such as tetraazacyclododecane-tetraacetic acid (DOTA) [24]. We hypothesized that the high density of carboxyl groups present at the nanoparticle surface would permit the formation of strong coordination bonds with the metal ion. Therefore, the nanoparticles were directly labelled with $^{68}$Ga under conditions commonly used for $^{68}$Ga-DOTA-complex formation (see experimental section). Unbound $^{68}$Ga was separated by size exclusion chromatography (FIG. 1(b)) yielding a labelling rate of 0.2 Mbq $^{68}$Ga per mg nanoparticles.

These results encouraged us to consider $^{111}$In as a further radiotracer which is used in gamma scintigraphy in conjunction with a metal chelator similarly to $^{68}$Ga. Simple co-incubation with polymer nanoparticles also resulted in effective labelling as shown in the chromatogram in FIG. 1(b).

Biodistrbution using PET and Gamma Scintigraphy: Biodistribution of labelled polymer nanoparticles was first investigated using $^{68}$Ga-labeling and PET-imaging on intravenously injected Wistar rats. For a more precise anatomical localization, the skeleton and metabolically active organs were also imaged in independent experiments using $^{18}$F-Fluoride and $^{18}$FDG as specific PET-tracers, respectively. In these experiments $^{18}$FDG was employed to reveal eyes, heart and kidney. Simultaneous visualization of the different image data was realized using Amira™ software. As shown in FIG. 1(a) $^{68}$Ga localized in the heart and also in a larger compartment that can be assigned to the liver. A smaller structure was also visible, representing the spleen. Interestingly, no signal was detected in the kidney suggesting no detectable renal elimination of the tracer. Since a significant part of the soluble tracer would be rapidly cleared from the blood stream through the renal system [31,32] we hypothesize from the absence of signal in kidney and bladder a strong association of the tracer with the nanoparticle during the observation period of one hour. One hour after injection PET showed an apparent similar organ distribution pattern with an overall weaker signal due to the short half-life of $^{68}$Ga ($t_{1/2}$=68 min, not shown).

Due to the particular high blood content in the heart and the liver it remained unclear whether the nanoparticles were taken up by these organs or actually resided in the blood fraction of these organs. Blood vessels were not visualized, most likely due to the dilution effect in the blood compartment and because of the relatively low resolution of this technique. A voxel size of 1 mm$^3$ is expected from our device according to the manufacturer. Therefore, strong signals originating from smaller structures such as most blood vessels are significantly weakened. To further analyze the blood compartment, gamma scintigraphy was performed after intravenous injection of $^{111}$In-labeled nanoparticles. FIG. 1(c) shows that after 15 minutes 75% of the injected activity was found in the blood and 21% in the liver. Considering that the liver contains 10-15% of the total blood amount we conclude that 10-13.5% of the injected material accumulated in the liver after 15 minutes. After one hour 45% remained in the blood and 40% was located in the liver, indicating increased clearance over time by the liver. The radioactivity remained relatively weak in the kidney and the bladder indicating a strong binding of the $^{111}$In to the polymer nanoparticles as was found for $^{68}$Ga.

Gd-labelling and MRI: Gd is a superparamagnetic contrast agent used in T1-weighted MRI [15] and as a trivalent cation in physiological condition. Clinical use is restricted to stable Gd-chelate complexes such as Gd-DTPA (Magnevist™) and requires intravenous injection of relatively high amounts of Gd, typically in the range of 40 mg Gd/kg body weight [25,26]. FIG. 2(a) shows that polymer nanoparticles could entirely adsorb nearly 1% Gd per mg lattice through a simple co-incubation step. Colloidal stability was maintained in HBSS when 10 times less Gd was used (FIG. 2(c)). In this case, the ξ-potential remained unchanged (FIG. 2(b)) indicating only a slight modification of physicochemical and colloidal properties of the polymer nanoparticles. In addition, labelled nanoparticles generated a strong MR contrast enhancement which was comparable to a Magnevist® solution containing 10 times more Gd (FIG. 2(d)). This apparent increase of contrast enhancement in the nanoparticle could be due to relatively high local concentrations of Gd$^{3+}$ ions within the negatively charged polymethacrylate network. Another reason could be a higher proton exchange rate caused by an increased inner hydration sphere around the Gd atoms [27].

Next, in vivo MR angiography was performed using the time-resolved fast TRICKS sequence which entails a subtraction of subsequent contrast-enhanced scans from a scan before application of contrast medium. Rats were intravenously injected with polymer nanoparticles loaded with 0.086% Gd containing a total amount of 21.5 µg Gd. Immediately after injection successive 30 seconds scans were performed and yielded a clear depiction of the abdominal aorta at the first scan, indicating the passage of labelled nanoparticles (FIG. 4(e,f)). It should be noted that in our experiments only 60 µg/kg Gd were applied which corresponds to about three orders of magnitudes less than the standard amount of Gd present in Magnevist® as used in MR angiography.

Interaction with e.g. blood cells: The obtained results indicated that the majority of the polymer nanoparticles were effectively circulating in the blood compartment within the first 15 minutes after injection. This raised the question whether circulation occurred in the soluble phase or alternatively, in association with particular blood components such as blood cells. Therefore, possible interactions with blood cells were investigated by flow cytometry using whole blood incubated with Rhodamine B-labelled nanoparticles. In preliminary experiments it was verified that Rhodamine B-labelling did not alter the physicochemical properties of the nanoparticles. FIG. 3(a) shows that after 5 minutes almost 10 percent of a subpopulation that can be assigned to thrombocytes and cell debris (G2, lower row) became marked with the nanoparticles. This process remained stable over a period of one hour under the experimental conditions. In addition, the labelled fraction further increased when higher amounts of nanoparticles were used, indicating that the adsorption process was not saturated in our experiment. In contrast, no increased fluorescence was assigned to erythrocytes (G1, upper row). Based on these observations it may be estimated that in the animal experiments about 440 million thrombocytes or debris entities were actually marked with the nanoparticles. Further experiments will be to identify the exact interaction mechanism. However, it can be expected that a strong association to the corpuscular components in blood, the cells, affects the fate of the nanoparticles and plays a role in the filtration process observed in the liver after one hour. Next, thrombocytes were distinguished from the cell debris in the analysed population through the analysis of CD42a expression. FIG. 3(b) shows that CD42a-positive cells became marked by the nanoparticles after 5 minutes. In contrast, no increase of Rhodamine B-fluorescence was observed in the CD42a-negative population containing the cell debris.

Finally, possible interactions with leucocytes were also investigated based on the expression of the common leukocyte antigen CD45 and the monocyte surface antigen CD14 (FIG. 3(c)). Flow cytometric analysis showed two CD45- positive subpopulations differing in their expression level. That with the lowest expression level became marked with the Rhodamine B-labelled nanoparticles. Moreover, the CD14-expressing cells were almost entirely labelled by the nanoparticles. These data show that interaction to cells is a selective process.

Cell interactions were further analysed by fluorescent microscopy using cultured mouse macrophages and human monocytes. FIG. 4(a) shows that the Rhodamine B-labelled nanoparticles (termed here as CL2) were internalized by macrophages and monocytes following incubation at 37° C. (two upper rows). However, at 4° C. a ring-like distribution surrounding the cell was observed indicating localization at the cell membrane. This demonstrates a cell uptake of polymer nanoparticles under physiological conditions through an active process, likely endocytosis. The interaction of nanoparticles with thrombocytes was further analysed by incubating the nanoparticles in whole blood. In this experiment, thrombocytes were subsequently fixed and erythrocytes lysed using a lysis buffer. In FIG. 4(b) (CL2, upper row) two thrombocytes are shown (bright field) that were identified through immunocytochemistry using the anti-CD42a antibody used for flow cytometry (FITC). One of both thrombocytes was clearly marked with the Rhodamine B-labelled nanoparticles. Moreover, the granular staining pattern suggests a localisation of the nanoparticles in the α granules as found in other studies using thorium dioxide or latex nanoparticles [42].

The size of nanoparticles and the chemical nature of their corona are critical properties influencing their interactions with living cells. To investigate the effect of these parameters in our system, Rhodamine B-labelled polymer nanoparticles (termed as CL6) with a smaller hydrodynamic diameter (52 nm) and carrying a similar, highly carboxylated corona were synthesised as well as similar nanoparticles with a hydrodynamic diameter of 62 nm and a corona containing both polymethacrylate and polyethylene glycol (PEG) at equimolarity (termed as CL13). Both types of nanoparticles were taken up by the macrophages and monocytes (FIG. 4(a)). In contrast, the thrombocytes internalized CL6 only (FIG. 4(b), demonstrating that cell uptake by these cells was prevented by the presence of PEG.

Figure 5:
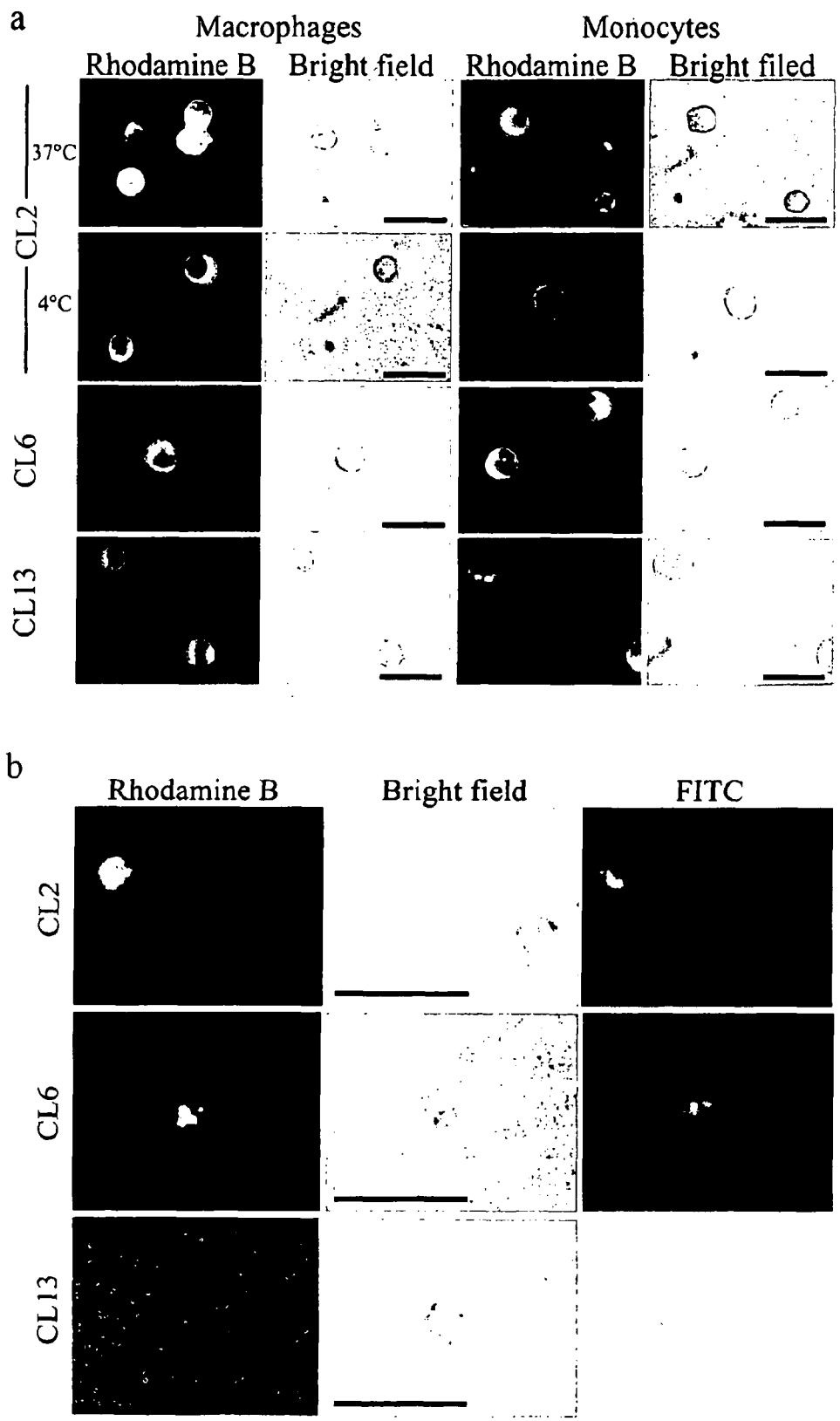

Characterization of nanoparticle-thrombocyte interactions: To further clarify the nature of this interaction, additional experiments using whole blood and flow cytometric analysis were performed. Pre-incubation of increasing amounts of unlabelled nanoparticles (EPS4, at 2 and 5 fold weight excess) inhibited the association of Rhodamine B-labelled nanoparticles to thrombocytes (CL2) (FIG. 5(a)), showing that interaction was a saturable process. In contrast, the postincubation of unlabelled nanoparticles did not displace the labelled nanoparticles from the cells demonstrating that cell association was irreversible (FIG. 5(b)). Furthermore, incubation at 4° C. apparently prevented cell association (FIG. 5(c)). This shows that the dilution step prior to the flow cytometric analysis apparently removes the nanoparticles from the cells if incubation occurs at 4° C. In a control experiment incubation was first performed at 4° C. and continued at room temperature. The same cell association was obtained compared to incubation only at room temperature (FIG. 5(d)) showing that the inhibition at 4° C. is reversible. Next, we wanted to know whether competitive binding experiments could be performed with thrombocytes and nanoparticles when incubated at 4° C. Flow cytometric histograms are shown in FIG. 5(e,f) and table 1 summarises a quantitative analysis based on three independent experiments. The whole blood was first incubated with Rhodamine B-labelled nanoparticles (CL2) and postincubated with increasing amounts of unlabelled nanoparticles (EPS4). When the competition experiment was performed at 4° C. the Rhodamine B-positive cells decreased from 39.60% without unlabelled nanoparticles to 27.60% and 17.53% after a postincubation using unlabelled nanoparticles with a weight excess of 2 and 5 fold, respectively. As a control, the experiment was performed at room temperature showing that the postincubation step did not affect the number of labelled cells. This in agreement with the previous displacement experiment shown in FIG. 5(b). We conclude that nanoparticles can be displaced from the thrombocyte surface at 4° C. using an appropriate competitor. This will be to determine the precise interaction partner responsible for internalization.

Together with the microscopic observation these data suggest a two-step association of nanoparticles with the thrombocytes, namely a passive and reversible interaction between the polymethacrylate corona and the thrombocyte surface and subsequently, internalization through an active process resulting in an intracellular granular localization.

Finally we wanted to know whether thrombocytes labelled with the nanoparticles are increasingly recognized by the leucocytes present in the blood. This could result in a fast elimination of these thrombocytes from the blood compartment. The whole blood was incubated with Rhodamine B-labelled nanoparticles and subsequently, stained with the FITC-labelled anti-CD42a antibody to detect the thrombocytes. Flow cytometric analysis was then performed on lysed blood and the cytometer was gated to the leucocytes in order to discriminate the thrombocytes. Under these conditions, CD42a-positive leucocytes can be assigned to leucocytes-thrombocytes co-aggregates or to leucocytes containing phagocytosed thrombocytes. FIG. 6(a) shows a control experiment without nanoparticles. In this case 9.69% of cells were CD 42a-positive corresponding to leucocytes associated with thrombocytes. Incubation of Rhodamine B-labelled nanoparticles did not change significantly this number (altogether 8.99%, FIG. 6(b)). Moreover, 1.18% of cells were both Rhodamine B- and CD 42a positive. This represents 15.11% of the total CD42a-positive cells and corresponds approximately to the loading rate of the thrombocytes under our experimental conditions. We thus conclude that the nanoparticles did not increase the association of thrombocytes to the blood leucocytes.

Figure 7:
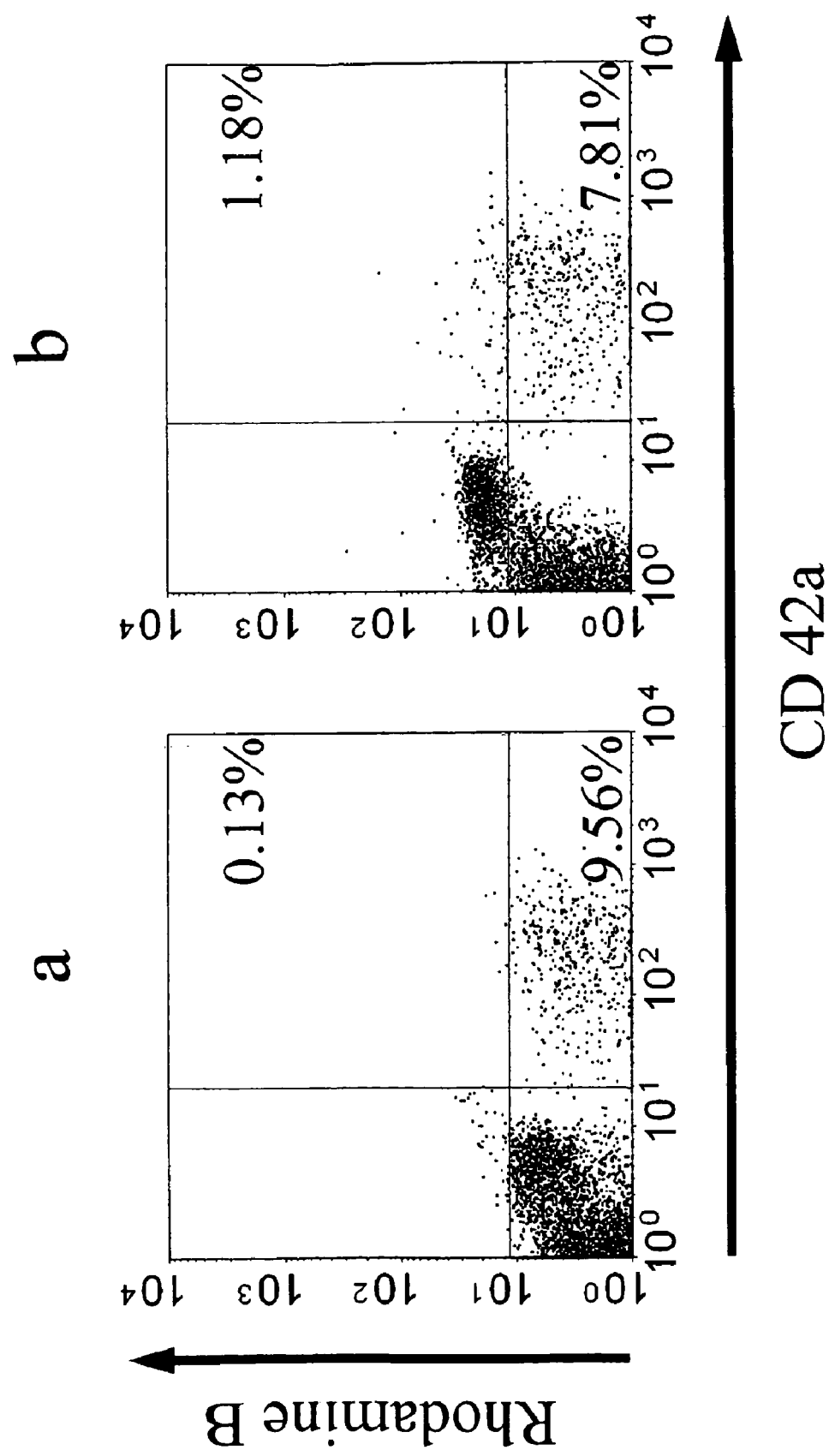
Figure 8:
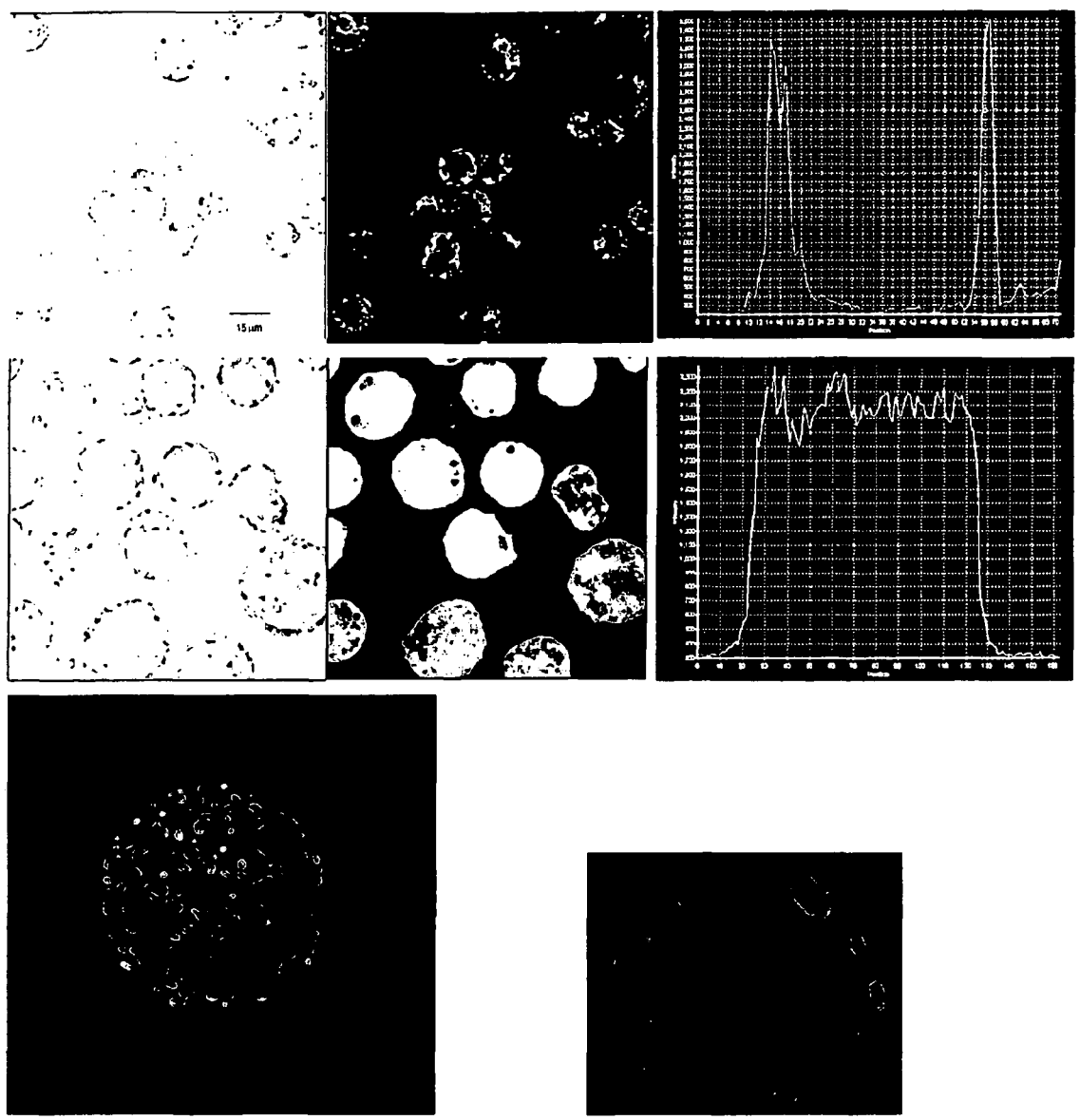

Understanding the behaviour of nanoparticles upon in vivo delivery is a critical issue in the development of multifunctional nanocarrier for diagnostic and therapeutic applications and requires appropriate and sensitive detection methods [28]. In this study we demonstrate the possibility to take advantage of PET, gamma scintigraphy, MRI and fluorescence detection to investigate the fate of polymer nanoparticles after intravenous delivery. A model can be derived in which a fraction of the nanoparticles rapidly associate to particular cells thereby circulating within the blood compartment. Subsequently, a displacement into the liver occurs which is in agreement with other studies showing effective elimination of colloidal carriers by the mononuclear phagocyte system [10,29,30]. This process is commonly attributed to adsorption of soluble blood factors on the particle surface leading to removal by macrophages or other phagocytotic cells [30]. In contrast, our results indicate that clearance of the three compartment polymer nanoparticle described in this report does not occur solely in the soluble phase, but in association with blood cells. Association with cell debris and erythrocytes were not detected. However, we found strong association to thrombocytes as well as to a CD45-positive leukocyte subpopulation and CD14-positive monocytes (FIGS. 7 & 8). These blood cell interactions with polymer particles appeared to be selective. To our best knowledge, this phenomenon has not been described in other reports before and thus opens up new opportunities for targeted drug delivery and cell therapy.

A characteristic of the three compartment polymer nanoparticles is the possibility to bind different tracers which can be used in different modalities of imaging and detection. To our knowledge, PET with labelled nanoparticles has only been reported with $^{64}$Cu for which the sources of supply remain limited [6,13]. In contrast, the polymer nanoparticles enable PET with the clinically well established radiotracer $^{68}$Ga. PET is a highly sensitive and non-invasive method allowing for a rapid whole body scan. On the other hand, MRI has the advantage of a higher temporal and spatial resolution and the acquisition of more precise anatomical information [33].

The biodistribution of nanoparticles has been investigated in numerous studies using T1-weigted MRI for nanoparticles with an iron oxide core for contrast enhancement [34-36]. For other nanoparticle types, e.g. polymer-based systems, Gd-labelling has been tested to enable T1-weighted MRI. Although effective labelling was reported, in vivo imaging studies encountered only limited success due to the low sensitivity of this method [15,27,37]. We showed that the three compartment polymer nanoparticle described in this report could adsorb ~0.1% Gd/mg lattice without detectable alterations of their physicochemical properties. In vivo imaging was realized and permitted visualization of the injected bolus in the blood compartment immediately after injection (FIG. 2(e)).

The ability to bind different cationic tracers is provided by the carboxyl groups of the dense polymethacrylate shell-corona structure of the given polymer nanoparticle. Therefore, we expect that other similar metal ions and isotopes, particularly with various half-life could be employed, thus adapting polymer nanoparticles to the major biomedical imaging techniques available today. These include $^{99m}$Tc, $^{67}$Ga and $^{123}$I used in Single Photon Computed Tomography (SPECT) or $^{60,61,64}$Cu for PET.

In addition, the described labelling concept could be also transferred to other types of nanoparticles, provided that a sufficiently dense polymethacrylate layer can be incorporated. Critical parameters influencing the biodistrbution of nanoparticles are their size, surface charge density, hydrophilicity and the chemical composition of both the core and the outer surface layer [6,38]. Polymer nanoparticles can be easily modified during the polymerization process. General physicochemical properties can be varied within a broad scale range and additional chemical substances can be included as exemplified with the Rhodamine B used in this study. Other components could be introduced to facilitate biodegradation or to incorporate pharmacological substances [39]. The outer layer can be further extended by the sequential addition of appropriate monomers to modulate the interaction to blood components or specific cells for targeted delivery and therapy.

TABLE 1

Dissociation of Rhodamine B-labelled polymer nanoparticles (CL2) from thrombocytes following the incubation with unlabelled particles (EPS4).

| Incubation steps | Positive cells |
|---|---|
| 5' 4° C. CL2 + 15' 4° C. 0x EPS4 + 30' RT | 39.60% |
| 5' 4° C. CL2 + 15' 4° C. 2x EPS4 + 30' RT | 27.60% |
| 5' 4° C. CL2 + 15' 4° C. 5x EPS4 + 30' RT | 17.53% |
| 5' RT CL2 + 15' RT 0x EPS4 + 30' RT | 54.50% |

TABLE 1-continued

Dissociation of Rhodamine B-labelled polymer nanoparticles (CL2) from thrombocytes following the incubation with unlabelled particles (EPS4).

| Incubation steps | Positive cells |
|---|---|
| 5' RT CL2 + 15' RT 2x EPS4 + 30' RT | 56.23% |
| 5' RT CL2 + 15' RT 5x EPS4 + 30' RT | 55.70% |

These data summarize the experiments shown in FIG. 5(e, f) (n=3). In the upper 3 experiments, the whole blood was first incubated during 5 minutes with CL2 at 4° C. to allow interaction with the cell surface. Subsequently, EPS4 was either omitted (0x) or added at 2 or 5 times weight excess to the mixture and further incubated for 15 minutes at 4° C. After another 30 minutes incubation step at room temperature the mixture was processed for flow cytometry analysis. Positive cells represent thrombocytes labelled with Rhodamine B-labelled nanoparticles. The lower three experiments are controls performed at room temperature (RT).

FIGS. 2-9 show the following:

FIG. 2: Radiolabelling of polymer nanoparticles and in vivo biodistribution following intravenous injection.
   (a) Wistar rats were injected intravenously with $^{68}$Ga-labeled nanoparticles and scanned using an animal-PET device after 15 minutes (yellow and red signal). For a rough anatomical assignment rats were treated in independent experiments with $^{18}$F-fluoride for skeleton and cartilage imaging (grey signal) and with $^{18}$F-deoxyglucose revealing eyes, heart and kidney (blue signal). The resulting data sets were 3D-reconstructed, superposed and aligned using Amira™. Two pictures from different angles are shown.
   (b) Elution profile of nanoparticle solutions after direct labelling with $^{63}$Ga or $^{111}$In. 95% of the loaded nanoparticles were collected in the fractions 6 to 8 (shaded region).
   (c) $^{111}$In-labelled nanoparticles were applied and radioactivity was measured in extracted organs and blood samples at indicated time points.

FIG. 3: Labelling of polymer nanoparticles with Gd and in vivo imaging using T1-weighted MRI.
   (a) Nanopartides were directly labelled with Gd through incubation with GdCl$_3$. The Gd-binding capacity was assessed using 37 mg nanoparticles. No detectable free Gd was found with up to 360 µg applied Gd.
   (b) ξ-potential of nanoparticles was measured at a Gd-content which showed no significant aggregation in HBSS.
   (c) Colloidal stability of Gd-labelled nanoparticles was assessed by DLS-measurements in water and HBSS.
   (d) T1-weighted MRI of phantoms containing the same Gd-labelled nanoparticles as in "b" with different Gd-amounts. Magnevist® was used for comparison.
   (e) & (f) For in vivo MRI Gd-labelled nanoparticles containing 0.086% Gd were applied similarly to FIG. 1 and rats were immediately scanned using the method of time-resolved imaging of contrast kinetics (TRICKS) over 30 seconds (e) as well as after 1 minute (f).

FIG. 4: Interaction of Rhodamine B-labelled polymer nanoparticles with blood components using flow cytometry.
   Rhodamine B-labelled nanoparticles were incubated with whole blood corresponding to previous in vivo-experiments. Representative data from three independent experiments are shown. Diluted whole blood was first analyzed by the scattered plot to distinguish between erythrocytes (G1) and thrombocytes plus cell debris (G2). Association of Rhodamine B-labelled nanoparticles to the gated cell components was then assessed at indicated time points. Controls correspond to t=0 (shaded histogram) (a). Thrombocytes were further distinguished from cell debris in G2 by CD42a expression analysis using a monoclonal FITC-labelled antibody. The control corresponds to t=0 (b). Similarly, interactions with leucocytes were analysed through CD45- or CD14 surface expression (c). In these experiments, erythrocytes were lysed prior to flow cytomerty. Controls are untreated cells.

FIG. 5: Influence of size and corona of polymer nanoparticles labelled with Rhodamine B on the cellular uptake by cultured cells (a) and thrombocytes from whole blood (b).

The sizes of the nanoparticles were 144 nm (CL2), 52 nm (CL6) and 62 nm (CL13). The corona of CL2 and CL6 was made out of methacrylic acid. The corona of CL13 was composed of a mixture of methacrylic acid and polyethylene glycol. Bright field and fluorescent images were taken after 20 minutes incubation time with macrophages and monocytes. Incubation temperature was 37'C, if not indicated. The whole blood was incubated with the nanoparticles for 10 minutes at room temperature and a FITC-labelled anti-CD42a antibody was added for additional 10 minutes to stain the thrombocytes. Staining was omitted in the case of CL13. Microscopic observations were done on lysed blood to remove the erythrocytes and fix the thrombocytes.

The scale bars correspond to 20 μm in the upper panel (a) and 5 μm in the lower panel (b).

Figure 6:
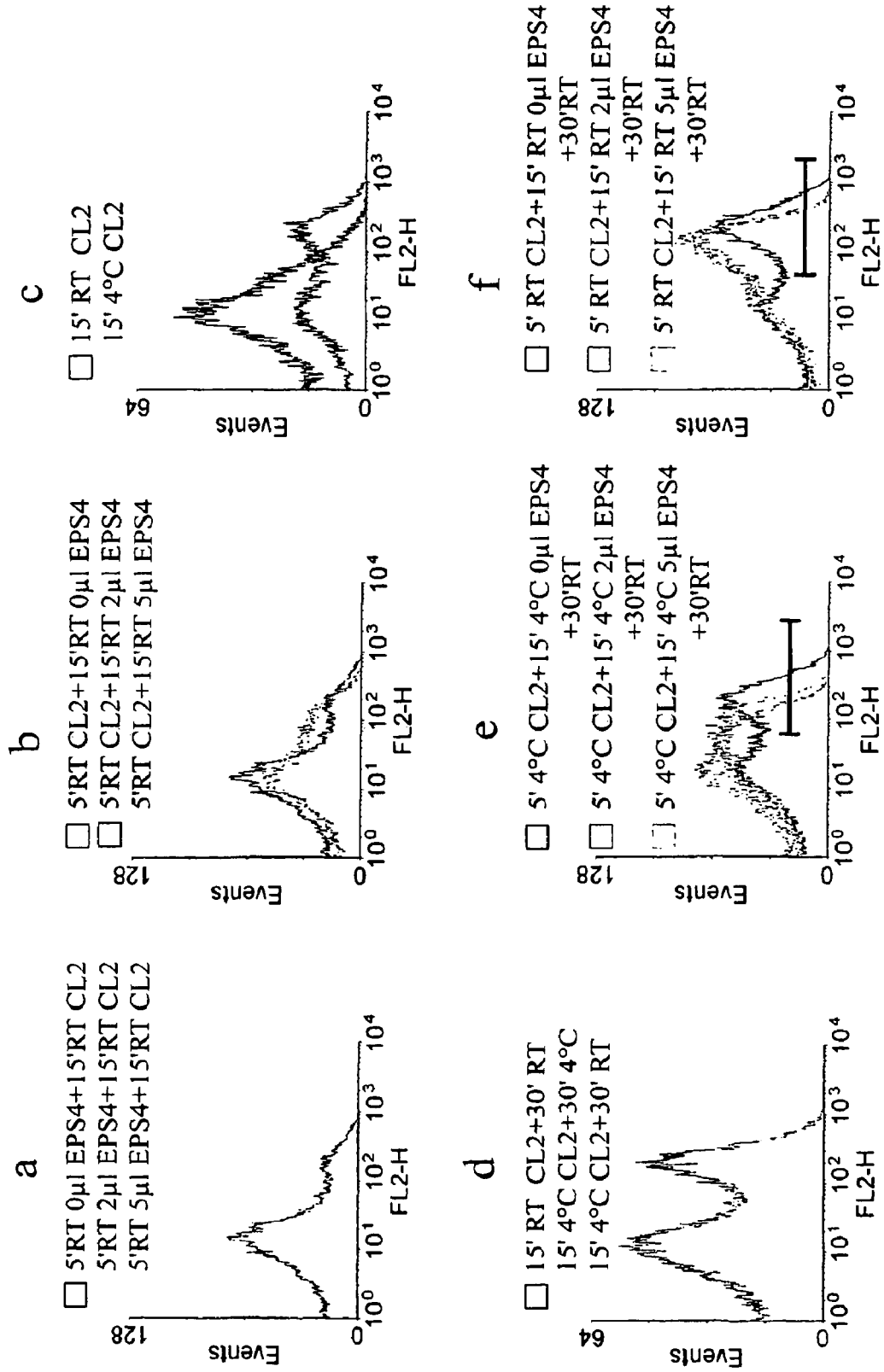

FIG. 6: Flow cytometric analysis to characterize polymer nanoparticle interaction with thrombocytes.

Whole blood was incubated as indicated with nanoparticles and cytometric analysis was performed on gated thrombocytes. Where indicated, sequential incubations with Rhodamine B labelled (CL2) and unlabelled (EPSA4) nanoparticles were performed in competition experiments. The influence of the incubation temperature on the cell association was assessed by performing sequential incubation steps at room temperature (RT) or 4° C. as depicted in the figure caption. The quantitative analysis of the competition experiments performed at 4° C. together with their corresponding control experiments performed at room temperature (e,f) is summarized in table 1.

FIG. 7: Influence of Rhodamine B-labelled polymer nanoparticles on the association of thrombocytes with blood leucocytes.

After incubation of the whole blood with Rhodamine B-labelled nanoparticles the thrombocytes were stained with FITC-labelled anti-CD42a antibody and flow cytometry was performed on gated leucocytes after removing erythrocytes with lysis buffer. CD 42a-positive cells are thus leucocytes associated with thrombocytes. These represent 9.69% of leucocytes in the control experiment (a) and 8.99% following incubation with the nanoparticles (b).

FIG. 8: Confocal microscopy of polymer nanoparticles interacting with peripheral blood monocytes Rhodamin labelled polymer nanoparticles bind instantaneously to the outer membrane of peripheral blood monocytes (upper panel).

Peripheral blood monocytes could be labelled with Calcein AM (middle panel). Calcein AM is a widely used green fluorescent cell marker. Calcein AM is membrane-permeable and thus can be introduced into cells via incubation, but fluorescence depend on a vital cell machinery.

On the left: native cells under normal transmission light; in the middle: cells under fluorescent light; on the right: colour distribution in a single cell—green (inside) and red (outside).

Single monocyte with rhodamin labelled polymer nanoparticles (lower panel). Left: 3-D view; right: section.

FIG. 9: Polymer nanoparticles bind to peripheral blood monocytes via CD14 receptor Peripheral blood monocytes are simultaneously labelled with CD14-FITC (green signal) and the rhodamin labelled polymer particles (red signal). Both fluorophores appear at the outer cell membrane and are partially co localized (yellow signal).

REFERENCES

[1] de Vries I J M et al. C G 2005 *Nat. Biotechnol.* 23, 1407-13
[2] Rockall A G et al 2005 *J. Clin. Oncol.* 23, 2813-21
[3] Cyrus T, Winter P M, Caruthers S D, Widdne S A and Lanza G 2005 *Expert Rev. Cardiovasc. Ther.* 3, 705-15
[4] Fahmy T M, Fong P M, Goyal A and Saltzman W M 2005 *Mat. Today* 8, 18-26
[5] Merisko-Liversidge E. Liversidge G G and Cooper E R 2003 *Eur. J. Pharm. Sci.* 18, 113-20
[6] Sun X, Rossin R, Turner J L, Becker M L, Joralemon M J, Welch M J and Wooley K L 2005 *Biomacromolecules* 6, 2541-54
[7] Zheng G, Chen J, Li H and Glickson J D 2005 *Proc. Natl. Acad. Sci. USA* 102, 17757-62
[8] Panyam J and Labhasetwar V 2004 *Curr. Drug Derry.* 1, 235-47
[9] Weissleder R, Kelly K, Sun E Y, Shtatland T and Josephson L 2005 *Nat. Biotechnot* 23, 1418-23
[10] Shenoy D, Little S, Langer R and Amiji M 2005 *Pharm. Res.* 12, 2107-14
[11] Bibby D C, Talmadge J E, Dalal M K, Kurz S G, Chytil K M, Barry S E, Shand D G and Steiert M 2005 *Int. J. Pharm.* 293, 281-90
[12] Maecke H R, Hofmann M and Haberkorn U 2005 *J. Nucl. Med.* 46, 172S-8S
[13] Rossin R, Pan D, Qi K, Turner J L, Sun X, Wooley K L and Welch M J 2005 *J. Nud. Med.* 46, 1210-8
[14] Jennewein M et al 2005 *Appl. Radiat. Isot.* 63, 343-51
[15] Turner J L, Pan D, Plummer R, Chen Z, Whittaker A K and Wooley K L 2005 *Adv. Fund. Mat.* 15, 1248-54
[16] Vuu K, Xie J, McDonald M A, Bernardo M, Hunter F, Zhang Y, U K. Bednarski M and Guccione S 2005 *Bioconjug. Chem.* 16, 995-9
[17] Härtig W, Paulke B R and Brückner G 1992 *Acta. Histochem.* 42, 261-5
[18] Härtig W, Pauke B R and Brückner G 1992 *J. Himforsch.* 33, 147-18
[19] Härtig W, Pauke B R and Brückner G 1992 *Acta Polym.* 43, 288-91
[20] Wang R, Schmiedel H and Pauke R B 2004 *Colloid Polym. Sci.* 283, 91-7
[21] Pauke B R, Möglich P M, Knippel E, Budde A, Nitzsche R and Müller R H 1995 *Langmuir* 11, 70-4
[22] Gouin S and Winnk F M 2001 *Bioconjugate Chem.* 12, 372-7
[23] Swan J S, Carroll T J, Kennell T W, Heisey D M, Korosec F R, Frayne R, Mistretta C A and Grist T M 2002 *Radiology* 225, 43-52

[24] Breeman W A, de Jong M, de Blois E, Bernard B F, Konijnenberg M and Kenning E P 2005 *Eur. J. Nucl. Med. Mol. Imaging* 32, 478-85
[25] Setser R M, O'Donnell T P, Smedira N G, Sabik J F, Halliburton S S, Stillman A E and White R D 2005 *Radiology* 237, 465-73
[26] Schlosser T, Hunold P, Herbom C U, Lehmkuhl H, Lind A, Massing S and Barkhausen J 2005 *Radiology* 236, 1041-6
[27] Parac-Vogt T N, Kmpe K, Laurent S, Piérart C, Elst L V, Muller R N and Binnemans K 2004 *Eur. J. Inorg. Chem.* 17, 3538-43
[28] LaVan D A, McGuire T and Langer R 2003 *Nat. Biotechnol.* 21, 1184-91
[29] Huang M, Wu W, Qian J, Wan D J, Wie X L and Zhu J H 2005 *Acta Pharmacol. Sin.* 26, 1512-8
[30] Gref R, Luck M, Quellec P, Marchand M, Dellacherie E, Harnisch S, Blunk T and Muller R H 2000 *Colloids Surf. B. Biointerfaces* 18, 301-13
[31] Sun Y, Anderson C J, Pajeau T S, Reichert D E, Hancock R D, Motekaitis R J, Martell A E and Welch M J 1996 *J. Med. Chem.* 39, 458-70
[32] Harris W H, Chen Y and Wein K 1994 *Inorg. Chem.* 33, 4991-8
[33] Degani H, Gusis V. Weinstein D, Fields S and Strano S 1997 *Nat. Med.* 3, 780-2
[34] Lewin M, Carlesso N, Tung C H, Tang X W, Cory D, Scadden D T and Weissleder R 2000 *Nat. Biotechnot* 18, 410-4
[35] Moore A, Marecos E, Jr A Bogdanov and Weissleder R 2000 *Radiology* 214, 568-74
[36] Huh Y M et al. 2005 *J. Am. Chem. Soc.* 127, 12387-91
[37] Morawski A M, Winter P M, Crowder K C, Caruthers S D, Fuhrhop R W, Scott M J, Robertson J D, Abendschein D R, Lanza G M and Wickline S A 2004 *Magn. Reson. Med.* 51, 480-6
[38] Gupta A K and Gupta M 2005 *Biomaterials* 26, 3995-4021
[39] Feng S S 2004 *Expert Rev. Med. Devices* 1, 115-25
[40] Yamamuro T, Nakamura T, Iida H, Kawanabe K, Matsuda Y, Ido K, Tamura J and Senaha Y 1998 *Biomaterials* 19, 1479-82
[41] Zurkova E, Bouchal K, Zdenkova D, Pelzbauer Z and Svec F 1983 *J. Polym. Sci: Polym. Chem. Ed* 21, 2949-60
[42] White J G 2005 *Platelets* 16, 121-31
[43] Svenson S and Tomalia D A 2005 *Adv. Drug Deliv. Rev.* 57, 2106-2129
[44] Yordanov A T, Kobayashi, H, English S J, Reijnders K, Milenic D, Krishna M C, Mitchell J B and Brechbiel M W 2003 *J. Mat. Chem.* 13, 1523-1525
[45] Yordanov A T, Lodder A L Woller E K, Cloninger M J, Patronas N, Milenic D, Brechbiel M W 2002 *Nano Letters* 2, 595-599
[46] Ishizu K 1998 Progress in Polymer Science, Vol. 23, pp. 1383-1408
[47] Reynolds C H et al. 2000 *J. Am. Chem. Soc.* 122, 8940-8945; and EP 1 031 354
[48] Leverge R, Rolland A 1987 *EP* 240 424

The invention claimed is:

1. Three compartment (core-shell-corona) polymer particles having a biocompatible polymeric corona as an outer layer and having an average diameter of between 20 nm and 900 nm said particles consisting of a polymeric core as an inner layer, a shell as an intermediary layer between said core and said corona, wherein
   a. the said shell has a hairy structure with carboxyl groups which
      (i) bind paramagnetic metal ions,
      (ii) bind opaque material and/or
      (iii) bind heavy metal isotopes,
   wherein
   b. said polymeric core comprises a polymer formed from homopolymers or copolymers with at least one compound selected from the group consisting of acrylic acid, methacrylic acid, methyl methacrylate, 2,3-epoxy-propyl-methacrylate, styrene, ethyl acrylate, butyl acrylate, 2-ethylhexyl acrylate, dimethylaminoethyl methacrylate, tert-butylaminoethyl methacrylate, hydroxyethyl methacrylate, hydroxypropyl methacrylate and/or vinylacetate, and
   wherein
   c. the said polymeric core is labelled via physical inclusion or chemical linkage or both using dye, fluorescence dye, or polycrystalline magnetic iron oxide, making these polymer particles suitable for optical imaging techniques, fluorescence activated cell identification and/or sorting, magnetic resonance and/or particle imaging techniques wherein
   d. the said corona is made from monomer units of acrylic acid or methacrylic acid alone or in combination thereof or in combination with monomers of hydroxyethyl acrylate or -methacrylate, or polyethylene glycol(PEG)-mono-methacylate.

2. Polymer particles according to claim 1 wherein the said corona is made of water soluble polymers resulting in colloidal stability in physiological environments.

3. Polymer particles according to claim 1, wherein side chains of the corona could be cross-linked via chemical activation.

4. Polymer particles according to claim 1, wherein the said corona assembles structures with specific affinity to cells or cellular components.

5. Polymer particles according to claim 1, wherein monomers or elements forming the shell contain carboxyl and/or hydroxyl groups.

6. The polymer particles of claim 1 wherein said homo- or copolymers were cross-linked using compound selected from the group consisting of allyl methacrylate (ALMA), ethylene glycol dimethacrylate (EGDMA), trimethylolpropane trimethacrylate (TMPTMA), divinyl benzene (DVB), glycidyl methacrylate, 2,2-dimethylpropane 1,3 diacrylate, 1,3-butylene glycol diacrylate, 1,3-butylene glycol dimethacrylate, 1,4-butanediol diacrylate, diethylene glycol diacrylate, diethylene glycol dimethacrylate, 1,6-hexanediol diacrylate, 1,6-hexanediol dimethacrylate, tripropylene glycol diacrylate, triethylene glycol dimethacrylate, tetraethylene glycol diacrylate, polyethylene glycol 200 diacrylate, tetraethylene glycol dimethacrylate, polyethylene glycol dimethacrylate, ethoxylated bisphenol A diacrylate, ethoxylated bisphenol A dimethacrylate, polyethylene glycol 600 dimethacrylate, poly(butanediol) diacrylate, trimethylolpropane triacrylate, trimethylolpropane trimethacrylate, pentaerythritol triacrylate, trimethylolpropane triethoxy triacrylate, glyceryl propoxy triacrylate, pentaerythritol tetraacrylate, pentaerythritol tetramethacrylate, and/or dipentaerythritol monohydroxypentaacrylate.

7. Polymer particles according to claim 1, wherein the total diameter is smaller than 900 nm.

8. Polymer particles according to claim 1, wherein the thickness of the corona is between 1 nm and 150 nm.

9. Polymer particles according to claim 1, wherein the proportion of the core to the total diameter is between 0.1 and 0.995.

10. A method of generating an image comprising
administering to a subject an image-enhancing agent according to claim 1, and
subjecting said subject to an image-forming procedure.

11. The method of claim 10 wherein said image forming procedure is a magnetic resonance and/or magnetic particle imaging procedure, x-ray imaging procedure, positron emission tomography procedure, gamma scintigraphy procedure, optical imaging procedure, fluorescence activated cell identification and/or sorting procedure, or a procedure that uses a combination of these imaging methods.

12. A medical diagnostic method for identifying diseases comprising administering to a subject an image enhancing agent according to claim 1, and subjecting said subject to an image forming procedure, wherein the diseases are diseases of the heart, the circulation, the brain and spinal cord, the bones and joints and cartilage, the lungs, the gastrointestinal tract including liver, spleen, stomach and bowel, pancreas, kidney, ureter, bladder, and the genitals.

13. A medical diagnostic method comprising administering to a subject an image enhancing agent according to claim 1, and subjecting said subject to an image forming procedure to identify and monitor neuromuscular diseases, immunological diseases, neoplastic diseases, haematological diseases, neurodegenerative diseases, and inflammatory diseases.

14. Polymer particles according to claim 4, wherein the said corona assembles structures with specific affinity to surfaces of peripheral blood cells.

15. Polymer particles according to claim 1, wherein the paramagnetic metal ion bound to said carboxyl groups in a. (i) is gadolinium, the opaque material bound to said carboxyl groups in a. (ii) are polyiodinated, brominated molecules, polymer chains or inorganic materials and/or the heavy metal isotopes bound to said carboxyl groups in a. (iii) are $^{68}$gallium or $^{111}$indium.

16. Polymer particles according to claim 15, wherein the inorganic materials are barium sulphate or other metals.

17. Polymer particles according to claim 7, wherein the total diameter is than 250 nm.

18. Polymer particles according to claim 7, wherein the total diameter is than 150 nm.

* * * * *